(12) United States Patent
Held et al.

(10) Patent No.: US 7,737,326 B2
(45) Date of Patent: *Jun. 15, 2010

(54) EPSPS PROMOTER FROM MAIZE

(75) Inventors: Bruce Marvin Held, Ames, IA (US); Herbert Martin Wilson, Ames, IA (US)

(73) Assignee: Midwest Oil Seeds Inc., Adel, IA (US)

( * ) Notice: Subject to any disclaimer, the term of this patent is extended or adjusted under 35 U.S.C. 154(b) by 273 days.

This patent is subject to a terminal disclaimer.

(21) Appl. No.: 11/117,965

(22) Filed: Apr. 29, 2005

(65) Prior Publication Data

US 2007/0061913 A1      Mar. 15, 2007

(51) Int. Cl.
*C12N 15/82* (2006.01)
*A01H 5/00* (2006.01)
*C07H 21/04* (2006.01)

(52) U.S. Cl. .................. 800/278; 800/298; 800/295; 435/320.1; 435/419; 435/468; 536/24.1

(58) Field of Classification Search .................. None
See application file for complete search history.

(56) References Cited

U.S. PATENT DOCUMENTS

| | | |
|---|---|---|
| 5,188,642 A | 2/1993 | Shah |
| 5,750,866 A | 5/1998 | Dietrich |
| 6,025,541 A | 2/2000 | Dietrich |
| 6,222,096 B1 | 4/2001 | Held |
| 6,420,630 B1 | 7/2002 | Wilson |
| 6,566,587 B1 | 5/2003 | Lebrun |
| 7,045,684 B1 * | 5/2006 | Held et al. .................. 800/300 |

OTHER PUBLICATIONS

Hemmings-Mieszczak et al. Alternative structures of the Cauliflower Mosaic Virus 35 S RNA leader: implications for viral expression and replication. (1997) J. Mol. Biol., vol. 267, pp. 1075-1088.*
Ma et al. ZMMBHe0005a21.f ZMMBHe *Zea mays* genomic clone ZMMBHe0005a21 5', genomic survey sequence. (2004) GenBank Accession CL988135, pp. 1-2.*
Whitelaw et al. OG95TH ZM_0.7_B *Zea mays* genomic clone ZMMBMa 0658022, genomic survey sequence. (2003) GenBank Accession CG224786, pp. 1-2.*
Klee et al. Cloning of an *Arabidopsis thaliana* gene encoding 5-enolpyruvylshikimate-3-phosphate synthase: seqeunce analysis and manipulation to obtain glyphosate-tolerant plants. (1987) Mol. Gen. Genet.; vol. 210; pp. 437-442.*

* cited by examiner

*Primary Examiner*—Cathy Kingdon Worley
(74) *Attorney, Agent, or Firm*—Emily E. Harris; Kent A. Herink

(57) ABSTRACT

The present invention is directed to a promoter, designated EPSP. The present invention is also directed to DNA molecules including the EPSP promoter, such as a DNA construct containing the promoter operably linked to one or more genes or antisense DNA. The invention is further directed to transformed plant tissue including the DNA molecule and to transformed plants and seeds thereof. The promoter is useful for driving gene or antisense expression for the purpose of imparting agronomically useful traits such as, but not limited to, increase in yield, disease resistance, insect resistance, herbicide tolerance, drought tolerance and salt tolerance in plants.

6 Claims, 2 Drawing Sheets

FIG. 1 : SEQ ID NO: 1

```
   1  CAACTCGAAA GGATCAAACT CTCCCTCTGG TTCGTTTGAC ATTGTGGATG
  51  GAGTGACTAA CCTGCTAACA CCCTGCAACA ATTTATACAG GAGCATATCC
 101  TCATGCACAC GCAAAACTGA TGTTGTCCAC AAGACACGCA CAGGACACGC
 151  ACAGGACACG CAAACAGTTT CAGACTCATG CACACGCACA TCAGTTTCAG
 201  ACTCAGGCAC ACGCACATCA AATCACCTTC GCTTGTCGAT GAGTCGCAGC
 251  CGCATCGTAC AATGGCGATT TTACCGACGA TAAGGCATGG GAGCACGAGC
 301  CGTCGCCGTC GCCTTGCGAG ACGACGGGAG CGATCTCTCC CTTCATTTAA
 351  TCTCTTCCAC GTCAGGTTAT TTTGCTGAGA TGGCAGTATA CAGACGGCAA
 401  AGTTAATGCC GTTGTACATG CCCTTAGACT CTTCCGTCAC CAACTCACTT
 451  AGATTTTTAC AACGGAACAT AAGGTTCGCT TGCAGACTTA CATATAAGGT
 501  ATAGTTGCAT AATAATCGCC TTATGCTGTA CATTGCGACA CCCGTAAATA
 551  TTCGATGAAA TATTAGTACA CAATATTAAA TAAGAACGAA CAATACATAT
 601  ATTATCATTG ATCTTAGTAT CTCCTTTTGC TCCTCGTAGA CAATTCTGT
 651  GTAAATTATG CGTAAAATTC GAGGACCAAA ACATTGGCTA GAAAAATACC
 701  TAAAATCAGT TTTGCAATTG TTTCTGATTT TCCTCATATT TTCTTGCTTA
 751  TAAAGTTTTC CAAAAGTACC ATTTTGGATG AAAAAACGGA AAACAACGCT
 801  GGTCTACTTG TAAATTTGGT AGTGACATTT GGGACCGTCT AGACACGACC
 851  TAAAAATAGT AGTCTAAAAC ATAGTCTGAC ACGATGCCTT AAAAATAGAC
 901  GACAAAGCAC AACACGATTA GATGTGTCGT GTTTTGACCG ACACGACACA
 951  AAGTAAGGCA CGATTTAAAA CCCAATAAAT AATATTTTAA TGGTTATTTT
1001  ATGTTCCAAT AATTTTCATC TCTTCAAAAA AATGTTATAG AAATCATTGA
1051  TACTTAGTTG AATATCCTAA CACAATATAT ATATATATAT TAATATATAT
1101  ATATATCAAT TTTAAGTCAC TTTGCTAGAC ATAGTAATAT ATTTTAAATA
1151  TTTTCTCTTT CTTGTATATT TTTAAAATAC ACATCAGTTT TTATATGTGT
1201  CGTGCTTGAA CCGACACGAT ATAATCATCG GTTCGCCGTA CTTCTAGATC
1251  ATGATGTTCC TAGGTTTTAA TATTAAGAGA CGGTCTATAT TAACTCAAAA
1301  CTATTTCGTG AAAGGCTAAC TCGAAAAAAA AATGAATGTA ATCACGGCCC
1351  GTCCTGGATT CGAGATTCTA ACGTTTCATT CGTGTCCAGT GTGCACACTT
1401  GTGGAAAAGG AAGACGAAGA AAAAAACCAA CAACTAACTC CGGCCCGCCG
```

1451 GATGCGCCCA CCTACTTCCC CCTCGCCCCT CTCATGGTCT CTCTCGCGCC

EPSPS PROMOTER FROM MAIZE

BACKGROUND OF THE INVENTION

This invention relates to a nucleic acid sequence isolate from corn and to methods of using the sequence. In particular, the invention relates to a nucleotide sequence derived from the EPSP corn synthase gene which is capable of directing constitutive expression of a nucleic acid sequence that is operably linked to the EPSP corn synthase sequence.

The selection of a promoter in the genetic engineering of a gene is often a critical factor in obtaining expression of the desired gene. Promoters are typically found at the 5' end of a gene which is either directly or indirectly recognized and bound by a DNA-dependent RNA polymerase during the initiation of transcription of the gene. Consequently, promoters play a major role in regulating gene expression. There are three general classes of promoters used in the genetic engineering of plants: 1) tissue specific promoters, 2) inducible promoters, and 3) constitutive promoters. Tissue specific or organ specific promoters drive gene expression is a certain tissue such as in the kernel, root, leaf, or tapetum of the plant. Chemicals or environmental stimuli such as heat, cold, or wounding induce inducible promoters. Although tissue specific and inducible promoters are required for certain applications, constitutive promoters are the most widely used promoters in the industry. Constitutive promoters are capable of driving a relatively high level of gene expression in most of the tissues of a plant. Constitutive promoters are particularly useful for producing herbicide tolerant plants. The most widely used constitutive promoter in the genetic engineering of plants is the CaMV 35S promoter. Other constitutive promoters include the maize polyubiquitin promoter and the rice actin promoter. In general, those familiar with the art agree that constitutive promoters that drive a high level of gene expression in most of the tissues of a plant are few in number and are of considerable value in the field of genetic engineering of crop plants.

Thus, it is desirable to develop additional constitutive promoters for use in plant transformation.

SUMMARY OF THE INVENTION

It is an object of the present invention to provide a strong, constitutive promoter which can effect high level expression of an operably linked gene or antisense DNA in transformed plants.

These and other objects of the present invention will become apparent to those skilled in the art upon reference to the following specification, drawings, and claims.

The present invention intends to overcome the difficulties encountered heretofore. To that end, a novel promoter, designated hce, is provided, comprising a nucleotide sequence as set forth in SEQ ID NO:1 is provided.

BRIEF DESCRIPTION OF THE DRAWINGS

FIG. 1 is the EPSP promoter sequence (hce).

DETAILED DESCRIPTION OF THE INVENTION

The present invention is directed to a promoter, designated hce. This promoter is from the EPSP corn synthase gene. The present invention is also directed to DNA molecules including the EPSPS promoter, such as a DNA construct comprising the promoter operably linked to one or more genes or antisense DNA. The invention is further directed to transformed plant tissue including the DNA molecule and to transformed plants and seeds thereof. The promoter is useful for driving gene or antisense expression for the purpose of imparting agronomically useful traits, such as increase in yield, disease resistance, insect resistance, herbicide tolerance, drought tolerance and salt tolerance in plants.

The EPSP corn synthase promoter is useful in regulating expression of a nucleic acid sequence of interest in monocots, specifically in corn (*zea mays*).

The present invention is described by reference to the following examples, which are not intended to limit the invention in any manner. Standard techniques well known in the art or the techniques specifically described below were utilized.

Example 1

Isolation of the Corn epsps Promoter

The promoter for the corn EPSPS gene was isolated using PCR (see FIG. 1 for sequence). The protocol was according to the specifications of the manufacturer QIAGEN. The template which was amplified was from a 6.0 kb corn genomic sequence. Primers were made which corresponded to the 5' end (CGGAATTCAACTCGAAAGGAT-CAAACTCTCCCTCTG) (SEQ ID No: 2) and 3' end (CGG-GATCCGCCGATGGTTGGTAGGGCGGGCGG) (SEQ ID NO: 3) of the region upstream of the putative start of translation of the epsps gene. The PCR primers included EcoRI and BamHI restriction sites respectively. These sites facilitated cloning the amplified fragment upstream of the bar gene and nos 3' terminator. The resulting expression cassette was in the vector pSB 11 which was combined with pSB 1 and mobilized into *Agrobacterium* LBA4404 via triparental mating and homologous recombination (U.S. Pat. No. 5,591,616). This plasmid in *Agrobacterium* was called hcebar and was used to transform corn immature embryos.

Example 2

The hcebar construct was introduced into immature corn embryos by *Agrobacterium*-mediated transformation. This was performed basically according to the protocol described in U.S. Pat. No. 6,420,630. The plasmid pSBhcebar carrying the promoter of the EPSP synthase gene (hce) driving the bar gene (bar) for resistance to bialaphos was introduced into *Agrobacterium tumefaciens* strain LBA4404, resulting in the super binary vectors as described in U.S. Pat. No. 5,591,616 (Hiei and Komari).

A glycerol stock of LBA4404 was then prepared. *Agrobacterium* was made ready for transformation experiments by removing a few flakes of frozen culture with a sterile loop, streaking it out on YP medium (5 g/l yeast extract, 10 g/l peptone, 5 g/l NaCl, and 15 g/l agar) containing 50 mg/l spectinomycin, and incubating it for one or two days at 28° C. When glycerol stocks were not used as the source, *Agrobacterium tumefaciens* maintained on YP plus spectinomycin at 4° C. was used to initiate new cultures of *Agrobacterium tumefaciens* that were grown as described above.

Immature corn embryos at an average length of about 1.2 mm (about ten days after pollination) were excised from Stine elite inbred 963. The embryos were immediately placed into 1 ml of liquid medium of the same composition as LS-inf medium—Ishida et al 1996—except that it contained 140 g/l sucrose instead of 68.5 g. This medium was labeled LS-infHS. After washing (after Ishida et al 1996) with fresh LS-infHS the embryos were immersed in LS-infHS medium containing 0.1 mM acetosyringone and a dispersed loopfull of the *Agrobacterium tumefaciens* strain LBA4404 carrying the hcebar construct. The embryos were then vortexed for 30 seconds and allowed to stand for 5 minutes (after Ishida et al, 1996). Co-cultivation was carried out at 19° as described in U.S. Pat. No. 6,420,630. Heat shock was applied after 46 to 50 hours as described in U.S. Pat. No. 6,420,630. After 3 days on co-cultivation medium the embryos were transferred to medium containing 1 mg/l bialaphos and 50 mg/l cefotaxime (DN62ALCB). After two 14 day passages on this medium, the embryos that developed embryogenic callus were transferred on to DN62ACB medium (containing 1 mg/l bialaphos and 250 mg/l cefotaxime). After this period putative transgenic events were transferred on to DN62B medium (as previous media but now no longer containing any silver nitrate or cefotaxime). Regeneration of transformed plants from these putative transgenic events was carried out exactly as described in U.S. Pat. No. 6,420,630.

Example 3

Regenerated plants were leaf painted with bialaphos and the presence of an expressing bar gene was confirmed. These plants were then selfed and seed collected. The seed was germinated and then the seedlings were sprayed with the agricultural herbicide Liberty. A 3:1 segregation ratio of resistant to sensitive seedlings was noted indicating Mendelian segregation of the transgene.

It is therefore demonstrated that the promoter from the corn EPSP synthase gene can drive expression of the bar gene.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

We claim:

1. An isolated nucleotide sequence comprising the corn EPSPS promoter of SEQ. ID. No. 1 operably linked to a heterologous nucleic acid.

2. An expression cassette comprising the nucleotide sequence of claim 1, wherein said expression cassette is either alone or in a vector.

3. A plant cell comprising the expression cassette of claim 2.

4. A mature plant comprising the nucleotide sequence of claim 1.

5. A method of expressing a nucleic acid sequence of interest in plants comprising the steps of:

(a) transforming a plant cell with the nucleic acid sequence of claim 1; wherein the sequence of interest is the heterologous nucleic acid of claim 1;

(b) regenerating a plant from said plant cell;

(c) allowing the transformed plant tissue to express said sequence of interest;

and (d) detecting such expression.

6. A nucleic acid construct comprising the sequence of claim 1.

* * * * *

SEQUENCE LISTING

<160> NUMBER OF SEQ ID NOS: 3

<210> SEQ ID NO 1
<211> LENGTH: 1500
<212> TYPE: DNA
<213> ORGANISM: Zea mays

<400> SEQUENCE: 1

```
caactcgaaa ggatcaaact ctccctctgg ttcgtttgac attgtggatg gagtgactaa      60
cctgctaaca ccctgcaaca atttatacag gagcatatcc tcatgcacac gcaaaactga     120
tgttgtccac aagacacgca caggacacgc acaggacacg caaacagttt cagactcatg     180
cacacgcaca tcagtttcag actcaggcac acgcacatca aatcaccttc gcttgtcgat     240
gagtcgcagc cgcatcgtac aatggcgatt ttaccgacga taaggcatgg gagcacgagc     300
cgtcgccgtc gccttgcgag acgacgggag cgatctctcc cttcatttaa tctcttccac     360
gtcaggttat tttgctgaga tggcagtata cagacggcaa agttaatgcc gttgtacatg     420
cccttagact cttccgtcac caactcactt agattttac aacggaacat aaggttcgct     480
tgcagactta catataaggt atagttgcat aataatcgcc ttatgctgta cattgcgaca     540
cccgtaaata ttcgatgaaa tattagtaca caatattaaa taagaacgaa caatacatat     600
attatcattg atcttagtat ctccttttgc tcctcgtaga acaattctgt gtaaattatg     660
cgtaaaattc gaggaccaaa acattggcta gaaaaatacc taaaatcagt tttgcaattg     720
tttctgattt tcctcatatt ttcttgctta taagtttttc caaaagtacc attttggatg     780
aaaaaacgga aaacaacgct ggtctacttg taaatttggt agtgacattt gggaccgtct     840
agacacgacc taaaaatagt agtctaaaac atagtctgac acgatgcctt aaaaatagac     900
gacaaagcac aacacgatta gatgtgtcgt gttttgaccg acacgacaca aagtaaggca     960
cgatttaaaa cccaataaat aatattttaa tggttatttt atgttccaat aatttttcatc    1020 tcttcaaaaa aatgttatag aaatcattga tacttagttg aatatcctaa cacaatatat    1080
atatatatat taatatatat atatatcaat tttaagtcac tttgctagac atagtaatat    1140
attttaaata ttttctcttt cttgtatatt tttaaaatac acatcagttt ttatatgtgt    1200
```

-continued

```
cgtgcttgaa ccgacacgat ataatcatcg gttcgccgta cttctagatc atgatgttcc    1260
taggttttaa tattaagaga cggtctatat taactcaaaa ctatttcgtg aaaggctaac    1320
tcgaaaaaaa aatgaatgta atcacggccc gtcctggatt cgagattcta acgtttcatt    1380
cgtgtccagt gtgcacactt gtggaaaagg aagacgaaga aaaaaaccaa caactaactc    1440
cggcccgccg gatgcgccca cctacttccc cctcgcccct ctcatggtct ctctcgcgcc    1500

<210> SEQ ID NO 2
<211> LENGTH: 36
<212> TYPE: DNA
<213> ORGANISM: Zea mays

<400> SEQUENCE: 2
cggaattcaa ctcgaaagga tcaaactctc cctctg                                36

<210> SEQ ID NO 3
<211> LENGTH: 32
<212> TYPE: DNA
<213> ORGANISM: Zea mays

<400> SEQUENCE: 3
cgggatccgc cgatggttgg tagggcgggc gg                                    32
```